(12) United States Patent
Takashima et al.

(10) Patent No.: US 8,410,234 B2
(45) Date of Patent: Apr. 2, 2013

(54) VINYL ETHER COMPOUND, VINYL ETHER POLYMER, AND METHOD FOR PRODUCING VINYL ETHER COMPOUND

(75) Inventors: Tsutomu Takashima, Tokyo (JP); Akira Shiibashi, Tokyo (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 0 days.

(21) Appl. No.: 13/393,982

(22) PCT Filed: Sep. 8, 2010

(86) PCT No.: PCT/JP2010/065421
§ 371 (c)(1),
(2), (4) Date: May 11, 2012

(87) PCT Pub. No.: WO2011/030792
PCT Pub. Date: Mar. 17, 2011

(65) Prior Publication Data
US 2012/0226008 A1 Sep. 6, 2012

(30) Foreign Application Priority Data

Sep. 8, 2009 (JP) ................. P2009-207406
Sep. 8, 2009 (JP) ................. P2009-207414
Sep. 10, 2009 (JP) ................. P2009-209498

(51) Int. Cl.
*C07C 43/188* (2006.01)
*C07C 41/16* (2006.01)
*C08F 36/20* (2006.01)

(52) U.S. Cl. ......... 526/282; 526/334; 568/664; 568/665

(58) Field of Classification Search ................. 526/282, 526/334; 568/664, 665
See application file for complete search history.

(56) References Cited

U.S. PATENT DOCUMENTS
4,375,004 A * 2/1983 Sprecker .............. 568/665

FOREIGN PATENT DOCUMENTS

| JP | 61-174208 | 8/1986 |
|---|---|---|
| JP | 61-287913 | 12/1986 |
| JP | 63-175010 | 7/1988 |
| JP | 1-102502 | 4/1989 |
| JP | 1-104606 | 4/1989 |
| JP | 1-168712 | 7/1989 |
| JP | 10-25262 | 1/1998 |
| JP | 10-251221 | 9/1998 |
| JP | 11-35735 | 2/1999 |
| JP | 11-80364 | 3/1999 |
| JP | 11-80433 | 3/1999 |
| JP | 11-91310 | 4/1999 |
| JP | 11-315171 | 11/1999 |
| JP | 2000-143732 | 5/2000 |
| JP | 2000-169523 | 6/2000 |
| JP | 2001-131289 | 5/2001 |
| JP | 2001-247722 | 9/2001 |
| JP | 2002-3429 | 1/2002 |
| JP | 2005-54016 | 3/2005 |
| JP | 2005-84584 | 3/2005 |
| JP | 2005-113049 | 4/2005 |
| JP | 2006-131805 | 5/2006 |
| JP | 2008-260915 | 10/2008 |

OTHER PUBLICATIONS

English language version of International Search Report for PCT/JP2010/065421, mailed Nov. 22, 2010.
English language translation of International Preliminary Report on Patentability for PCT/JP2010/065421, mailed Apr. 19, 2012.

\* cited by examiner

*Primary Examiner* — Fred M Teskin
(74) *Attorney, Agent, or Firm* — Greenblum & Bernstein, P.L.C.

(57) ABSTRACT

A vinyl ether compound represented by formula (1-a) or formula (1-b):

[Chemical Formula 1]

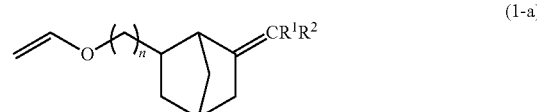

(1-a)

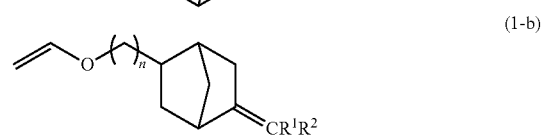

(1-b)

wherein n represents 0 or 1, and $R^1$ and $R^2$ each independently represent a hydrogen atom, a methyl group, or an ethyl group, provided that a total of the number of carbon atoms of $R^1$ and the number of carbon atoms of $R^2$ is 1 or 2.

15 Claims, No Drawings

VINYL ETHER COMPOUND, VINYL ETHER POLYMER, AND METHOD FOR PRODUCING VINYL ETHER COMPOUND

TECHNICAL FIELD

The present invention relates to a vinyl ether compound, a vinyl ether polymer, and a method for producing a vinyl ether compound.

BACKGROUND ART

Conventionally, as acrylate compounds for obtaining acrylate-based polymers having an alicyclic skeleton structure, dimethyloltricyclopentadecane di(meth)acrylate, pentacyclopentadecanedimethyl di(meth)acrylate, and the like are disclosed (for example, see patent literature 1 to 4).

In addition, as vinyl ether compounds for obtaining vinyl ether-based polymers having an alicyclic skeleton structure, polyfunctional vinyl ether obtained by converting an OH group in the methylol group of tricyclodecanedimethylol to vinyl ether (see patent literature 5), 3,4-bis(2-vinyloxyethyloxy)tricyclo[5.2.1.0$^{2,6}$]decane (see patent literature 6), tricyclodecanemonomethyl vinyl ether derived from tricyclodecanemonomethanol, tricyclodecane vinyl ether derived from tricyclodecanemonol, or pentacyclopentadecane monovinyl ether derived from pentacyclopentadecanemonol (see patent literature 7), and the like are disclosed.

In addition, conventionally, as alicyclic vinyl ether polymers, a vinyl ether polymer having a tricyclodecane or pentacyclopentadecane skeleton (see patent literature 7 and 8), a vinyl ether polymer having a norbornenyl skeleton (see patent literature 9), and the like are disclosed.

Further, in recent years, for the purpose of the modification of rubber, studies of introducing a polyisobutylene skeleton into a rubber composition have been made. For example, as a method for improving wet grip properties for tires, a method for mixing an elastomer having a polyisobutylene skeleton into a rubber material for tires is known, and as such a method, methods using a rubber composition comprising acid anhydride-modified polybutene (see patent literature 10), a rubber composition comprising a polyisobutylene compound having an alkoxysilyl group (see patent literature 11 and 12), a rubber composition comprising an isobutylene-based polymer having a stable free radical in a molecule (see patent literature 13), a rubber composition comprising a block copolymer of a homopolymer or copolymer of a diene compound with polybutene (see patent literature 14 and 15), a rubber composition for tire tread comprising a brominated polyisobutylene/p-methylstyrene copolymer and a rubber component (see patent literature 16), a rubber composition containing a styrene-isobutylene copolymer in a rubber component (see patent literature 17 and 18), a rubber composition in which polyisobutylene having a mercapto group or the like is mixed (see patent literature 19), polyisobutylene having a disulfide bond at least in part (see patent literature 20), and the like are proposed.

CITATION LIST

Patent Literature

[Patent Literature 1] Japanese Patent Application Laid-Open Publication No. 61-174208
[Patent Literature 2] Japanese Patent Application Laid-Open Publication No. 61-287913
[Patent Literature 3] Japanese Patent Application Laid-Open Publication No. 63-175010
[Patent Literature 4] Japanese Patent Application Laid-Open Publication No. 01-168712
[Patent Literature 5] Japanese Patent Application Laid-Open Publication No. 10-025262
[Patent Literature 6] Japanese Patent Application Laid-Open Publication No. 2002-003429
[Patent Literature 7] Japanese Patent Application Laid-Open Publication No. 2005-113049
[Patent Literature 8] Japanese Patent Application Laid-Open Publication No. 2006-131805
[Patent Literature 9] Japanese Patent Application Laid-Open Publication No. 2008-260915
[Patent Literature 10] Japanese Patent Application Laid-Open Publication No. 11-35735
[Patent Literature 11] Japanese Patent Application Laid-Open Publication No. 11-91310
[Patent Literature 12] Japanese Patent Application Laid-Open Publication No. 12-169523
[Patent Literature 13] Japanese Patent Application Laid-Open Publication No. 12-143732
[Patent Literature 14] Japanese Patent Application Laid-Open Publication No. 11-80364
[Patent Literature 15] Japanese Patent Application Laid-Open Publication No. 13-131289
[Patent Literature 16] Japanese Patent Application Laid-Open Publication No. 11-80433
[Patent Literature 17] Japanese Patent Application Laid-Open Publication No. 11-315171
[Patent Literature 18] Japanese Patent Application Laid-Open Publication No. 2001-247722
[Patent Literature 19] Japanese Patent Application Laid-Open Publication No. 10-251221
[Patent Literature 20] Japanese Patent Application Laid-Open Publication No. 2005-54016

SUMMARY OF INVENTION

Technical Problem

It is an object of the present invention to provide a new vinyl ether compound, vinyl ether polymer, and method for producing a vinyl ether compound.

Solution to Problem

The present invention provides a vinyl ether compound represented by formula (1-a) or formula (1-b):

[Chemical Formula 1]

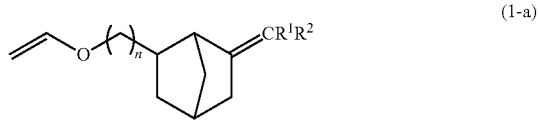

(1-a)

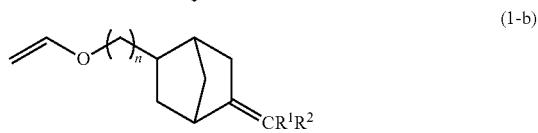

(1-b)

wherein n represents 0 or 1, and $R^1$ and $R^2$ each independently represent a hydrogen atom, a methyl group, or an ethyl group, provided that a total of the number of carbon atoms of $R^1$ and the number of carbon atoms of $R^2$ is 1 or 2.

In the vinyl ether compound according to the present invention, n may be 0. In addition, it is possible that $R^1$ and $R^2$ are each independently a hydrogen atom or a methyl group, and the total of the number of carbon atoms of $R^1$ and the number of carbon atoms of $R^2$ is 1.

The present invention also provides a vinyl ether polymer comprising a structural unit represented by formula (2-a) and/or a structural unit represented by formula (2-b):

[Chemical Formula 2]

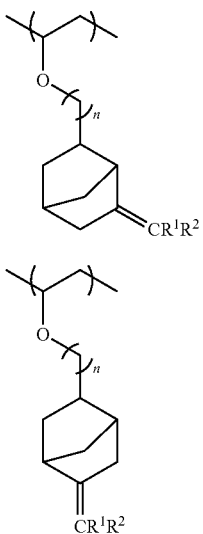

(2-a)

(2-b)

wherein n represents 0 or 1, and $R^1$ and $R^2$ each independently represent a hydrogen atom, a methyl group, or an ethyl group, provided that a total of the number of carbon atoms of $R^1$ and the number of carbon atoms of $R^2$ is 1 or 2.

In the vinyl ether polymer according to the present invention, n may be 0. In addition, it is possible that $R^1$ and $R^2$ are each independently a hydrogen atom or a methyl group, and the total of the number of carbon atoms of $R^1$ and the number of carbon atoms of $R^2$ is 1.

A polymerization degree of the vinyl ether polymer according to the present invention can be 2 to 10000. In addition, a weight-average molecular weight of the vinyl ether polymer according to the present invention can be 400 to 1000000.

The vinyl ether polymer according to the present invention may further comprises a structural unit represented by formula (3). Such a vinyl ether polymer has sufficient crosslinkability, and therefore is useful in introducing a polyisobutylene skeleton into a rubber composition.

[Chemical Formula 3]

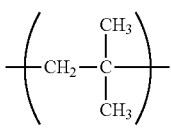

(3)

The present invention further provides a method for producing a vinyl ether compound, comprising a first step of hydrolyzing a compound obtained by reaction of a norbornene compound represented by formula (4) with a carboxylic acid represented by formula (5) in the presence of an acid catalyst, to obtain a norbornanol compound represented by formula (6-a) or formula (6-b); and a second step of vinylating a hydroxyl group of the above norbornanol compound to obtain a vinyl ether compound represented by formula (1-c) or formula (1-d),

[Chemical Formula 4]

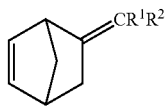

(4)

wherein $R^1$ and $R^2$ each independently represent a hydrogen atom, a methyl group, or an ethyl group, provided that a total of the number of carbon atoms of $R^1$ and the number of carbon atoms of $R^2$ is 1 or 2,

[Chemical Formula 5]

$R^5$—$CO_2H$ (5)

wherein $R^5$ represents an alkyl group having 1 to 20 carbon atoms,

[Chemical Formula 6]

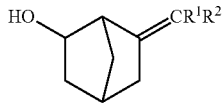

(6-a)

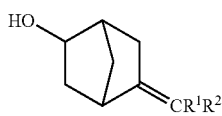

(6-b)

wherein $R^1$ and $R^2$ each independently represent a hydrogen atom, a methyl group, or an ethyl group, provided that a total of the number of carbon atoms of $R^1$ and the number of carbon atoms of $R^2$ is 1 or 2,

[Chemical Formula 7]

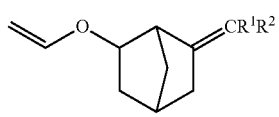

(1-c)

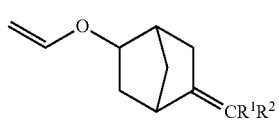

(1-d)

wherein $R^1$ and $R^2$ each independently represent a hydrogen atom, a methyl group, or an ethyl group, provided that a total of the number of carbon atoms of $R^1$ and the number of carbon atoms of $R^2$ is 1 or 2.

In the method for producing a vinyl ether compound according to the present invention, it is possible that $R^1$ and $R^2$ are each independently a hydrogen atom or a methyl group, and the total of the number of carbon atoms of $R^1$ and the number of carbon atoms of $R^2$ is 1.

Advantageous Effects of Invention

According to the present invention, a new vinyl ether compound, vinyl ether polymer, and method for producing a vinyl ether compound are provided.

The vinyl ether compound of the present invention is useful in producing a resin useful in the field of optical materials excellent in transparency and electrical conductivity. In addition, a resin obtained from the vinyl ether compound of the present invention exhibits excellent performance also in electronic and electrical fields of semiconductor sealing materials, insulating coating materials, and the like. Further, the vinyl ether compound of the present invention has less skin irritancy and odor, and is better in workability in a resin production process, compared with the acrylate compounds described in patent literature 1 to 4. In addition, acrylate-based polymers obtained from the acrylate compounds described in patent literature 1 to 4 have moisture absorbency, and therefore have a problem with dimensional stability when used as industrial materials, whereas the resin obtained from the vinyl ether compound of the present invention has low moisture absorbency, and is excellent in moisture resistance.

The vinyl ether polymer of the present invention is a curable resin cured by ultraviolet rays, electron beams, heat, and the like, and is excellent in rapid curability. In addition, the vinyl ether polymer of the present invention is excellent in transparency and electrical conductivity and therefore is useful in the field of optical materials, and can exhibit excellent performance also in electronic and electrical fields of semiconductor sealing materials, insulating coating materials, and the like. In addition, acrylate-based polymers conventionally often used as curable resins have moisture absorbency, and therefore have a problem with dimensional stability when used as industrial materials. On the other hand, the vinyl ether polymer of the present invention has low moisture absorbency, and is excellent in moisture resistance. In addition, the vinyl ether polymer of the present invention further comprising the structural unit represented by formula (3) has sufficient crosslinkability, and therefore is useful in introducing a polyisobutylene skeleton into a rubber composition.

DESCRIPTION OF EMBODIMENTS

Preferred embodiments of a vinyl ether compound, a method for producing a vinyl ether compound, and a vinyl ether polymer according to the present invention will be described below.

[Vinyl Ether Compound]

A vinyl ether compound according to this embodiment is a compound represented by formula (1-a) or formula (1-b). With such a vinyl ether compound, a vinyl ether polymer comprising a structural unit represented by formula (2-a) and/or a structural unit represented by formula (2-b) can be obtained.

[Chemical Formula 8]

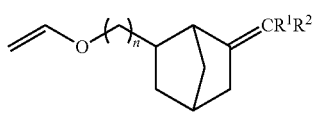

(1-a)

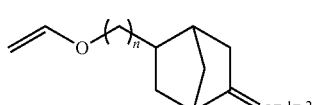

(1-b)

[Chemical Formula 9]

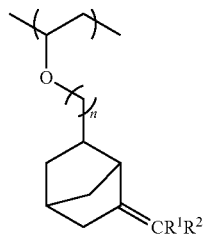

(2-a)

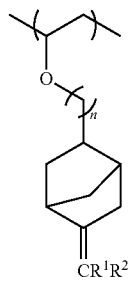

(2-b)

wherein n represents 0 or 1, and $R^1$ and $R^2$ each independently represent a hydrogen atom, a methyl group, or an ethyl group, provided that the total of the number of carbon atoms of $R^1$ and the number of carbon atoms of $R^2$ is 1 or 2.

If n is 2 or more, a result is that in the vinyl ether polymer obtained from the vinyl ether compound, a norbornane skeleton considered to provide heat resistance and low moisture absorbency is away from a polymer main chain. Therefore, if n is 2 or more, there is a tendency that a decrease in the heat resistance and an increase in the moisture absorbency of the vinyl ether polymer are caused, and the thermal stability and shape retention properties of the vinyl ether polymer are poor, compared with a case where n is 0 or 1.

n is preferably 0, and at this time, the vinyl ether polymer is better in heat resistance and shape retention properties.

n being 0 indicates that an oxygen atom and a norbornane skeleton in the formulas are directly bonded to each other. The vinyl ether compound in which n is 0 is represented by formula (1-c) or formula (1-d). In the formulas, $R^1$, $R^2$, and n have the same meanings as the above.

[Chemical Formula 10]

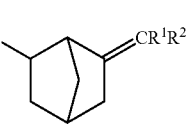

(1-c)

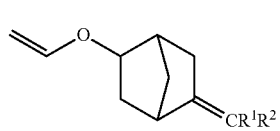

(1-d)

There are isomers represented by formula (1-a-1), formula (1-a-2), formula (1-b-1), and formula (1-b-2), for the vinyl ether compound according to this embodiment, and all isomers have the above-described effect. The vinyl ether compound may be any one of these isomers, or may be a mixture of a plurality of isomers.

[Chemical Formula 11]

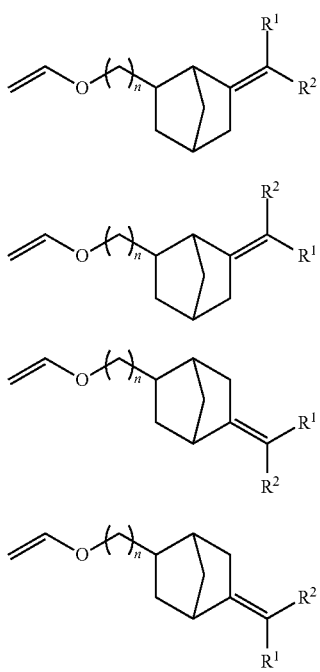

(1-a-1)

(1-a-2)

(1-b-1)

(1-b-2)

The vinyl ether compound according to this embodiment can be produced, for example, by the following method.

(1) Method for Producing Vinyl Ether Compound in which n is 0

The vinyl ether compound in which n is 0 (the vinyl ether compound represented by formula (1-c) or formula (1-d)) can be produced, for example, by a production method comprising the following first step and the second step.

(1-1) First Step

In the first step, a compound obtained by the reaction of a norbornene compound represented by formula (4) with a carboxylic acid represented by formula (5) in the presence of an acid catalyst is hydrolyzed to obtain a norbornanol compound represented by formula (6-a) or formula (6-b). In the formulas, $R^1$ and $R^2$ have the same meanings as the above, and $R^5$ represents an alkyl group having 1 to 20 carbon atoms.

[Chemical Formula 12]

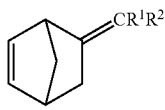

(4)

[Chemical Formula 13]

$R^5—CO_2H$ (5)

[Chemical Formula 14]

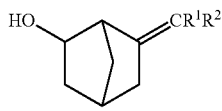

(6-a)

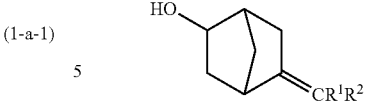

(6-b)

The first step can be performed, for example, as follows. First, as shown in the following scheme 1, the norbornene compound represented by formula (4) is reacted with the carboxylic acid represented by formula (5) in the presence of an acid catalyst to obtain a compound represented by formula (4-a) and/or an ester compound represented by formula (4-b).

Scheme 1

[Chemical Formula 15]

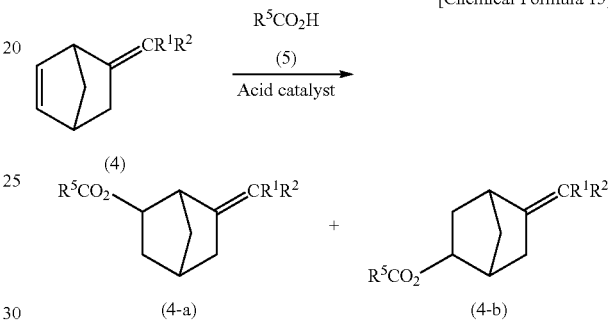

Here, examples of the carboxylic acid represented by formula (5) include formic acid, acetic acid, butyric acid, isobutyric acid, valeric acid, isovaleric acid, hydroangelic acid, pivalic acid, and caproic acid, and among these, formic acid or acetic acid is preferred in terms of steric hindrance in an addition reaction, odor, cost, and the like. In other words, examples of $R^5$ include a hydrogen atom, a methyl group, an ethyl group, a n-propyl group, an isopropyl group, a n-butyl group, an isobutyl group, a sec-butyl group, a tert-butyl group, and a pentyl group, and among these, a hydrogen atom or a methyl group is preferred.

The used amount of the compound represented by formula (5) in the reaction shown in the scheme 1 is preferably 1 to 10 moles, more preferably 2 to 5 moles, with respect to 1 mole of the norbornene compound represented by formula (4) which is a reaction raw material.

Examples of the acid catalyst includes sulfuric acid, formic acid, phosphoric acid, toluenesulfonic acid, boron trifluoride, a boron trifluoride-ether complex, boron trifluoride hydrate, and acidic resins, and among these, sulfuric acid is preferred in terms of acidity, cost, and the like.

The used amount of the acid catalyst in the reaction shown in the scheme 1 is preferably 0.1 to 50% by mass, more preferably 1 to 25% by mass, with respect to the entire reaction mixture.

The reaction shown in the scheme 1 is preferably performed in the presence of a solvent. Examples of the solvent include aromatic hydrocarbon solvents, such as toluene, benzene, chlorobenzene, and xylene; aliphatic hydrocarbon solvents, such as propane, n-butane, isobutane, n-pentane, isopentane, n-hexane, n-heptane, n-octane, isooctane, decane, and hexadecane; halogenated hydrocarbon solvents, such as methylene chloride and carbon tetrachloride; and ether solvents, such as diethyl ether, dibutyl ether, tetrahydrofuran, and dioxane. Among these, toluene and benzene are preferred in terms of a boiling point, and the solubility of the acid catalyst and the reaction substrate. These may be used alone, or two or more may be mixed and used.

The reaction temperature of the reaction shown in the scheme 1 is preferably 20° C. to 150° C., more preferably 50° C. to 120° C. In addition, the reaction time of the reaction shown in the scheme 1 is preferably 30 minutes to 12 hours, more preferably 2 hours to 5 hours.

Following the reaction shown in the scheme 1, the ester compounds represented by formula (4-a) and/or formula (4-b) are hydrolyzed to obtain norbornanol compounds represented by formula (6-a) and/or formula (6-b), as shown in the following scheme 2. The ester compound represented by formula (4-a) and the ester compound represented by formula (4-b) may be simultaneously subjected to hydrolysis, as shown in the following scheme 2, or may each be independently subjected to hydrolysis.

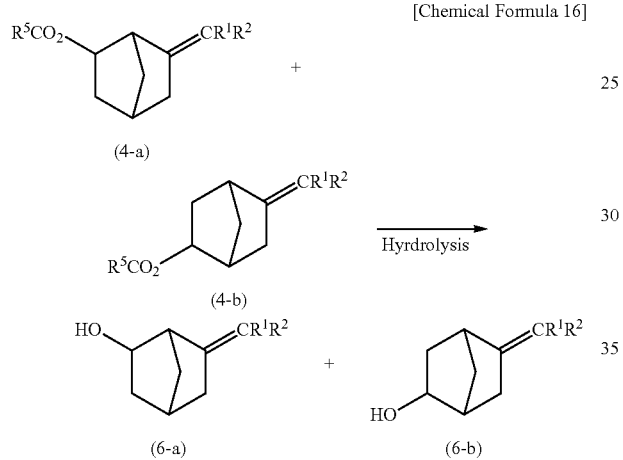

Scheme 2

[Chemical Formula 16]

(4-a)

(4-b)

Hyrdrolysis (6-a)

(6-b)

Here, the hydrolysis can be performed by various publicly known methods. As the hydrolysis, hydrolysis in the presence of a base is preferred. Examples of the base include potassium hydroxide, sodium hydroxide, lithium hydroxide, cesium hydroxide, rubidium hydroxide, and barium hydroxide. The used amount of the base in the hydrolysis is preferably 1.0 to 5.0 moles, more preferably 2.0 to 4.0 moles, with respect to 1.0 mole of the compounds represented by formula (4-a) and/or formula (4-b).

The hydrolysis is generally performed in the presence of a solvent. Examples of the solvent include methanol, ethanol, 2-propanol, butanol, and tetrahydrofuran. Among these, methanol and ethanol are preferred in terms of a boiling point, separation from the products, and the solubility of the base.

As the reaction conditions of the hydrolysis, reaction temperature is preferably 0° C. to 100° C., more preferably 50° C. to 90° C. In addition, reaction time is preferably 30 minutes to 24 hours, more preferably 1 hour to 4 hours.

In the first step, the reaction shown in the scheme 1 and the reaction shown in the scheme 2 may each be independently performed. In addition, it is possible to perform the reaction shown in the scheme 1, and then perform hydrolysis by a method such as adding the base and the solvent to a reaction solution without isolating the ester compounds represented by formula (4-a) and/or formula (4-b) from the reaction solution.

(1-2) Second Step

In the second step, the hydroxyl groups of the norbornanol compounds represented by formula (6-a) and/or formula (6-b) are vinylated to obtain the vinyl ether compounds represented by formula (1-c) and/or formula (1-d).

The second step can be performed, for example, as follows. As shown in a scheme 3, the norbornanol compounds represented by formula (6-a) and/or formula (6-b) are reacted with a vinyl ester compound represented by formula (7) in the presence of an Ir catalyst to obtain the vinyl ether compounds represented by formula (1-c) and/or formula (1-d). The norbornanol compound represented by formula (6-a) and the norbornanol compound represented by formula (6-b) may be simultaneously subjected to a vinylation reaction, as shown in the following scheme 3, or may each be independently subjected to a vinylation reaction.

Scheme 3

[Chemical Formula 17]

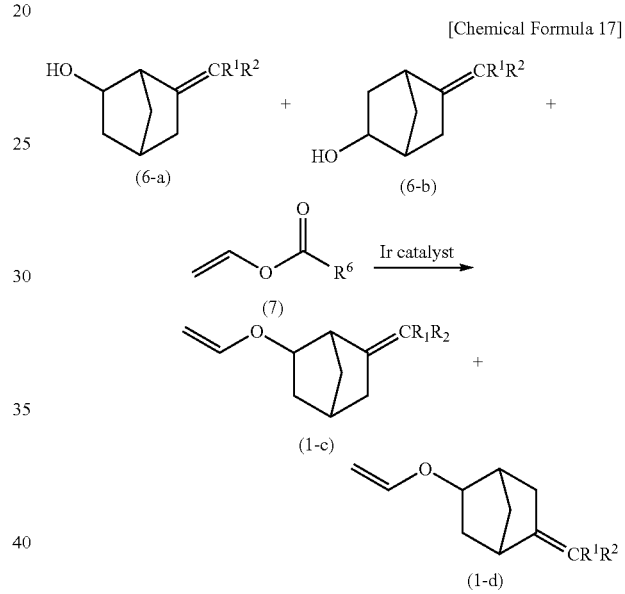

(6-a)

(6-b)

(7)

Ir catalyst (1-c)

(1-d)

wherein $R^6$ is an alkyl group having 1 to 20 carbon atoms. Examples of $R^6$ include a methyl group, an ethyl group, a normal propyl group, an isopropyl group, a n-butyl group, an isobutyl group, a sec-butyl group, and a tert-butyl group, and among these, a methyl group is preferred.

Examples of the Ir catalyst include organometallic complexes, such as a di-μ-chlorobis[η-cycloocta-1,5-diene)iridium(I)] catalyst (hereinafter abbreviated as an $[IrCl(cod)]_2$ catalyst; cod represents cycloocta-1,5-diene), $[Ir(cod)_2]BF_4$, $[Ir(cod)_2(CH_3CN)]BF_4$, and $IrCl(CO)(PPh_3)_2$ (Ph represents a phenyl group), and inorganic iridium compounds, such as metal iridium, iridium oxide, iridium hydroxide, and iridium fluoride, and among these, $[IrCl(cod)]_2$ is preferred in terms of reactivity and stability.

The reaction shown in the scheme 3 is preferably performed in the presence of a solvent. Examples of the solvent include aliphatic hydrocarbon solvents, such as hexane, heptane, and octane; alicyclic hydrocarbon solvents, such as cyclohexane; aromatic hydrocarbon solvents, such as benzene, toluene, xylene, and ethylbenzene; halogenated hydrocarbon solvents, such as chloroform, dichloromethane, and 1,2-dichloroethane; ether solvents, such as diethyl ether, dimethoxyethane, tetrahydrofuran, and dioxane; ketone solvents, such as acetone and methyl ethyl ketone; ester solvents, such as methyl acetate, ethyl acetate, isopropyl acetate, and butyl acetate; amide solvents, such as N,N-dimethylformamide and N,N-dimethylacetamide; and nitrile solvents, such as acetonitrile, propionitrile, and benzonitrile. These may be used alone, or two or more may be mixed and used.

In the reaction shown in the scheme 3, it is preferred to add a base in order to increase reaction rate. Here, examples of the base include alkali metal hydroxides, such as sodium hydroxide and potassium hydroxide; alkaline-earth metal hydroxides, such as magnesium hydroxide, calcium hydroxide, and barium hydroxide; alkali metal carbonates, such as lithium carbonate, sodium carbonate, potassium carbonate, and cesium carbonate; alkaline-earth metal carbonates, such as magnesium carbonate; alkali metal hydrogen carbonates, such as lithium hydrogen carbonate, sodium hydrogen carbonate, potassium hydrogen carbonate, and cesium hydrogen carbonate; alkali metal organic acid salts (particularly, alkali metal acetates), such as lithium acetate, sodium acetate, potassium acetate, and cesium acetate; alkaline-earth metal organic acid salts, such as magnesium acetate; alkali metal alkoxides, such as lithium methoxide, sodium methoxide, sodium ethoxide, sodium isopropoxide, and potassium ethoxide; alkali metal phenoxides, such as sodium phenoxide; amines (tertiary amines and the like), such as triethylamine and N-methylpiperidine; and nitrogen-containing aromatic heterocyclic compounds, such as pyridine, 2,2'-bipyridyl, and 1,10-phenanthroline. Among the above bases, bases containing sodium are preferred.

The used amount of the base is preferably 0.001 to 3 moles, more preferably 0.005 to 2 moles, with respect to 1 mole of the norbornanol compounds represented by formula (6-a) and/or formula (6-b) which are reaction raw materials.

The reaction temperature of the reaction shown in the scheme 3 can be appropriately selected according to the types of the reaction components and the catalyst, and the like, but is preferably 20° C. to 170° C., more preferably 70° C. to 120° C. In addition, the reaction time of the reaction shown in the scheme 3 can be appropriately selected depending on the types of the reaction components and the catalyst, or the reaction temperature, but is preferably 2 hours to 24 hours, more preferably 5 hours to 15 hours.

The reaction shown in the scheme 3 may be performed at atmospheric pressure, or may be performed under reduced pressure or under applied pressure. The atmosphere of the reaction is not particularly limited unless it inhibits the reaction, and it may be, for example, any of an air atmosphere, a nitrogen atmosphere, and an argon atmosphere. In addition, the reaction can be performed by any method, such as a batch method, a semibatch method, or a continuous method.

In the reaction shown in the scheme 3, the used amount of the compound represented by formula (7) which is a reaction raw material is preferably 1 mole to 5 moles, further preferably 2 to 3 moles, with respect to 1 mole of the norbornanol compound represented by formula (6-a) or formula (6-b).

In addition, the second step can also be performed by the following method. In other words, it is also possible to obtain the vinyl ether compounds represented by formula (1-c) and/or formula (1-d) by reacting the norbornanol compounds represented by formula (6-a) and/or formula (6-b) with acetylene in the presence of a base to vinylate the hydroxyl groups of the norbornanol compounds, as shown in the following scheme 4. The norbornanol compound represented by formula (6-a) and the norbornanol compound represented by formula (6-b) may be simultaneously subjected to a vinylation reaction, as shown in the following scheme 4, or may each be independently subjected to a vinylation reaction.

Scheme 4

[Chemical Formula 18]

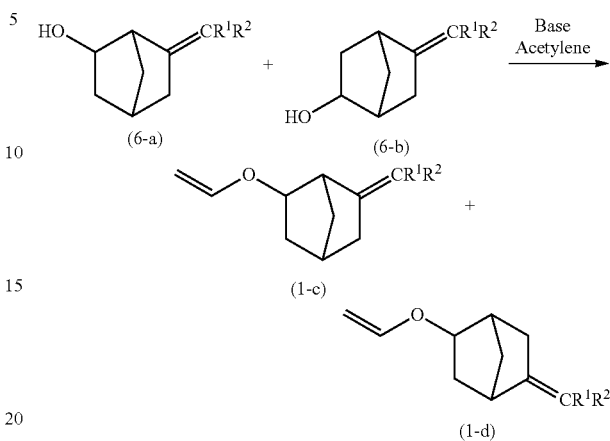

The reaction shown in the scheme 4 can be performed in the presence of a solvent or without a solvent. Here, examples of the solvent include aprotic solvents, such as 1,3-dimethyl-2-imidazolidinone, diglyme, triglyme, and tetraglyme. These may be used alone, or two or more may be mixed and used.

The used amount of the aprotic solvent is preferably 1 to 20 moles, more preferably 3 to 13 moles, with respect to 1 mole of the norbornanol compounds represented by formula (6-a) and/or formula (6-b).

In the reaction shown in the scheme 4, examples of the base include alkali metal hydroxides, such as sodium hydroxide and potassium hydroxide; and alkaline-earth metal hydroxides, such as magnesium hydroxide, calcium hydroxide, and barium hydroxide, and among these, alkali metal hydroxides, such as sodium hydroxide and potassium hydroxide, are preferred.

The used amount of the base is preferably 0.05 to 1 mole with respect to 1 mole of the norbornanol compounds represented by formula (6-a) and/or formula (6-b), and more preferably 0.1 to 0.5 moles from reaction rate and economical viewpoints.

The acetylene used in the scheme 4 is preferably introduced into a reaction container so that gauge pressure is 0.01 MPa or more, and is more preferably introduced into a reaction container so that gauge pressure is 0.15 MPa or more, in terms of reaction rate and yield.

The reaction temperature of the reaction shown in the scheme 4 is preferably 80 to 180° C., more preferably 100 to 140° C.

(2) Method for Producing Vinyl Ether Compound in which n is 1

The vinyl ether compound in which n is 1 can be produced, for example, by a production method comprising the following first step, the following second step, and the following third step.

(2-1) First Step

In the first step, aldehyde compounds represented by formula (8-a) and/or formula (8-b) are obtained from the norbornene compound represented by formula (4). In the formulas, $R^1$ and $R^2$ have the same meanings as the above.

[Chemical Formula 19]

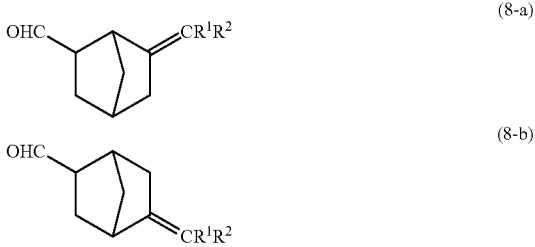

The first step can be performed, for example, as follows. First, as shown in the following scheme 5, the norbornene compound represented by formula (4) is reacted in the presence of a metal catalyst under an atmosphere of a mixed gas containing carbon monoxide and hydrogen, to obtain the aldehyde compounds represented by formula (8-a) and/or formula (8-b).

Scheme 5

[Chemical Formula 20]

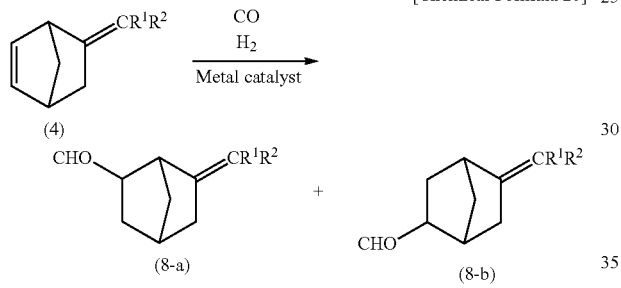

Here, as the metal catalyst, a transition metal compound is used, and particularly, compounds of Group 8 elements, Group 9 elements, and Group 10 elements in the periodic table are useful. Among them, cobalt compounds, rhodium compounds, iridium compounds, ruthenium compounds, platinum compounds, and the like are useful.

As a metal complex, a halide, oxide, carboxylate, and nitrate of cobalt or rhodium, or complexes having olefins, hydrogen, carbon monoxide, tertiary amines, phosphite, phosphinite, phosphonite, phosphine, and the like, and chelating polydentate ligands thereof are preferred. These transition metal compounds can be used alone or by adding another metal compound as a promoter.

The used amount of the metal catalyst in the reaction shown in the scheme 5 is preferably 0.00001 to 0.1 moles, more preferably 0.0001 to 0.01 moles, with respect to 1 mole of the norbornene compound represented by formula (4). In the reaction shown in the scheme 5, when 1000 to 10000 moles of the ligand is added with respect to 1 mole of the catalyst, it is possible to provide advantages, such as the control of the partial pressure of the catalyst, a decrease in reaction pressure, and an improvement in selectivity.

The reaction temperature of the reaction shown in the scheme 5 is preferably 30 to 300° C., further preferably 50 to 250° C. The reaction pressure of the reaction shown in the scheme 5 is preferably 20 to 250 atmospheres, and the mixing ratio of carbon monoxide to hydrogen (the volume of carbon monoxide/the volume of hydrogen) in the mixed gas used is preferably in the range of 0.5 to 2.0, further preferably in the range of 0.8 to 1.2.

In addition, the reaction shown in the scheme 5 can be performed in the presence of a solvent. Examples of the solvent include saturated hydrocarbon solvents, aromatic hydrocarbon solvents, such as benzene, ether solvents, alcohol solvents, ester solvents, sulfolane, and water. These may be used alone, or two or more may be mixed and used. In addition, in the reaction shown in the scheme 5, it is also possible to use the reaction raw material and the reaction products as the solvent.

(2-2) Second Step

In the second step, the carbonyl groups of the aldehyde compounds represented by formula (8-a) and/or formula (8-b) are reduced to obtain alcohol compounds represented by formula (9-a) and/or formula (9-b).

[Chemical Formula 21]

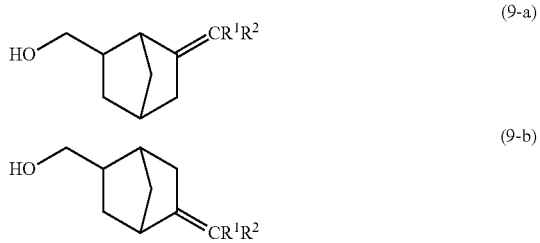

The second step can be performed, for example, as follows. As shown in a scheme 6, the aldehyde compounds represented by formula (8-a) and/or formula (8-b) are reacted with a metal hydride to obtain the alcohol compounds represented by formula (9-a) and/or formula (9-b). The aldehyde compound represented by formula (8-a) and the aldehyde compound represented by formula (8-b) may be simultaneously subjected to a reduction reaction, as shown in the following scheme 6, or may each be independently subjected to a reduction reaction.

Scheme 6

[Chemical Formula 22]

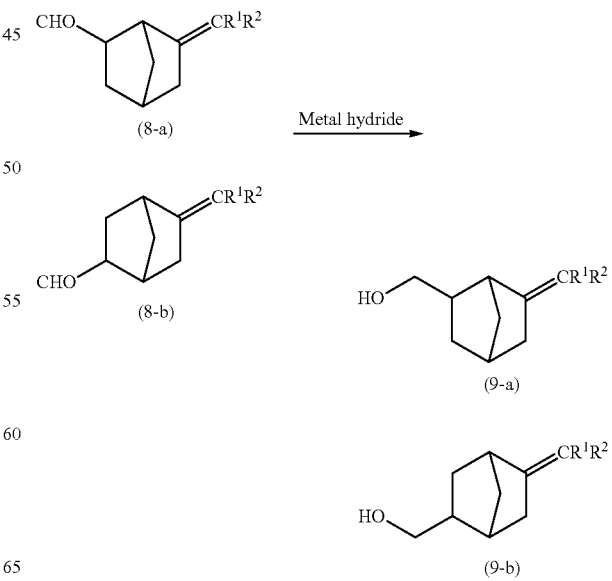

As the reduction reaction of the aldehyde compounds represented by formula (8-a) and/or formula (8-b), publicly known various methods can be used, but a method using a metal hydride is preferred. Examples of the metal hydride include lithium aluminum hydride, sodium boron hydride, lithium boron hydride, and diisobutylaluminum hydride.

The used amount of the metal hydride in the reaction shown in the scheme 6 is preferably 0.25 to 3 moles, more preferably 1 to 2 moles, with respect to 1 mole of the compounds represented by formula (8-a) and/or formula (8-b) which are reaction raw materials.

The reaction shown in the scheme 6 is generally performed in the presence of a solvent. The solvent can be appropriately selected according to the metal hydride used. For example, when lithium aluminum hydride is used as the metal hydride, ether solvents, such as diethyl ether and tetrahydrofuran, are preferred in terms of the solubility of lithium aluminum hydride.

The reaction temperature of the reaction shown in the scheme 6 is preferably 0° C. to 70° C., further preferably 20° C. to 70° C. In addition, reaction time is preferably 30 minutes to 24 hours, further preferably 1 hour to 5 hours.

(2-3) Third Step

In the third step, the hydroxyl groups of the alcohol compounds represented by formula (9-a) and/or formula (9-b) are vinylated to obtain vinyl ether compounds represented by formula (1-e) and/or formula (1-f).

[Chemical Formula 23]

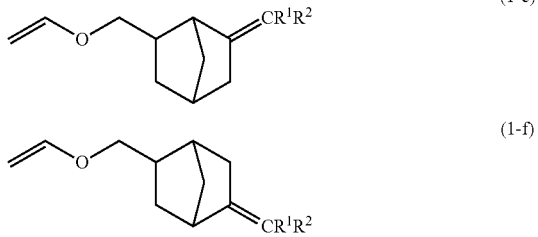

The third step can be performed, for example, as follows. As shown in the following scheme 7, the alcohol compounds represented by formula (9-a) and/or formula (9-b) are reacted with the vinyl ester compound represented by formula (7) in the presence of an Ir catalyst to obtain the vinyl ether compounds represented by formula (1-e) and/or formula (1-f). The alcohol compound represented by formula (9-a) and the alcohol compound represented by formula (9-b) may be simultaneously subjected to a vinylation reaction, as shown in the following scheme 7, or may each be independently subjected to a vinylation reaction.

Scheme 7

[Chemical Formula 24]

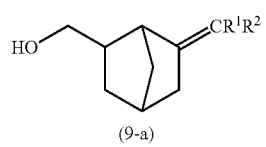

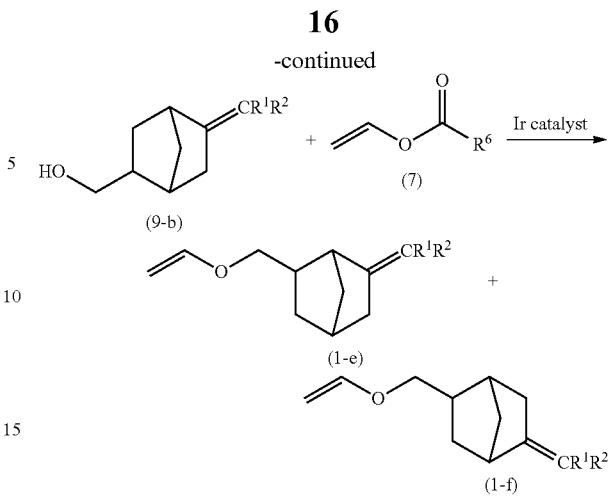

The reaction shown in the scheme 7 can be performed under conditions similar to those of the reaction shown in the above scheme 3. In other words, $R^6$ in formula (7) is an alkyl group having 1 to 20 carbon atoms, and examples of the alkyl group include a methyl group, an ethyl group, a normal propyl group, an isopropyl group, a n-butyl group, an isobutyl group, a sec-butyl group, and a tert-butyl group, and among these, a methyl group is preferred.

Examples of the Ir catalyst include organometallic complexes, such as a di-μ-chlorobis[(η-cycloocta-1,5-diene)iridium(I)] catalyst (hereinafter abbreviated as an $[IrCl(cod)]_2$ catalyst; cod represents cycloocta-1,5-diene), $[Ir(cod)_2]BF_4$, $[Ir(cod)_2(CH_3CN)]BF_4$, and $IrCl(CO)(PPh_3)_2$ (Ph represents a phenyl group), and inorganic iridium compounds, such as metal iridium, iridium oxide, iridium hydroxide, and iridium fluoride, and among these, $[IrCl(cod)]_2$ is preferred in terms of reactivity and stability.

The reaction shown in the scheme 7 is preferably performed in the presence of a solvent. Examples of the solvent include aliphatic hydrocarbon solvents, such as hexane, heptane, and octane; alicyclic hydrocarbon solvents, such as cyclohexane; aromatic hydrocarbon solvents, such as benzene, toluene, xylene, and ethylbenzene; halogenated hydrocarbon solvents, such as chloroform, dichloromethane, and 1,2-dichloroethane; ether solvents, such as diethyl ether, dimethoxyethane, tetrahydrofuran, and dioxane; ketone solvents, such as acetone and methyl ethyl ketone; ester solvents, such as methyl acetate, ethyl acetate, isopropyl acetate, and butyl acetate; amide solvents, such as N,N-dimethylformamide and N,N-dimethylacetamide; and nitrile solvents, such as acetonitrile, propionitrile, and benzonitrile. These may be used alone, or two or more may be mixed and used.

In the reaction shown in the scheme 7, it is preferred to add a base in order to increase reaction rate. Here, examples of the base include alkali metal hydroxides, such as sodium hydroxide and potassium hydroxide; alkaline-earth metal hydroxides, such as magnesium hydroxide, calcium hydroxide, and barium hydroxide; alkali metal carbonates, such as lithium carbonate, sodium carbonate, potassium carbonate, and cesium carbonate; alkaline-earth metal carbonates, such as magnesium carbonate; alkali metal hydrogen carbonates, such as lithium hydrogen carbonate, sodium hydrogen carbonate, potassium hydrogen carbonate, and cesium hydrogen carbonate; alkali metal organic acid salts (particularly, alkali metal acetates), such as lithium acetate, sodium acetate, potassium acetate, and cesium acetate; alkaline-earth metal organic acid salts, such as magnesium acetate; alkali metal alkoxides, such as lithium methoxide, sodium methoxide, sodium ethoxide, sodium isopropoxide, and potassium ethoxide; alkali metal phenoxides, such as sodium phenoxide; amines (tertiary amines and the like), such as triethylamine and N-methylpiperidine; and nitrogen-containing aromatic heterocyclic compounds, such as pyridine, 2,2'-bipyridyl, and 1,10-phenanthroline. Among the above bases, bases containing sodium are preferred.

The used amount of the base is preferably 0.001 to 3 moles, more preferably 0.005 to 2 moles, with respect to 1 mole of the alcohol compounds represented by formula (9-a) and/or formula (9-b) which are reaction raw materials.

The reaction temperature of the reaction shown in the scheme 7 can be appropriately selected according to the types of the reaction components and the catalyst, and the like, but is preferably 20° C. to 170° C., more preferably 70° C. to 120° C. In addition, the reaction time of the reaction shown in the scheme 7 can be appropriately selected depending on the types of the reaction components and the catalyst, or the reaction temperature, but is preferably 2 hours to 24 hours, more preferably 5 hours to 15 hours.

The reaction shown in the scheme 7 may be performed at atmospheric pressure, or may be performed under reduced pressure or under applied pressure. The atmosphere of the reaction is not particularly limited unless it inhibits the reaction, and it may be, for example, any of an air atmosphere, a nitrogen atmosphere, and an argon atmosphere. In addition, the reaction can be performed by any method, such as a batch method, a semibatch method, or a continuous method.

In the reaction shown in the scheme 7, the used amount of the compound represented by formula (7) which is a reaction raw material is preferably 1 mole to 5 moles, further preferably 2 to 3 moles, with respect to 1 mole of the alcohol compounds represented by formula (9-a) and/or formula (9-b).

In addition, the third step can also be performed under conditions similar to those of the reaction shown in the above scheme 4. In other words, it is also possible to obtain the vinyl ether compounds represented by formula (1-e) and/or formula (1-f) by reacting the alcohol compounds represented by formula (9-a) and/or formula (9-b) with acetylene in the presence of a base to vinylate the hydroxyl groups of the alcohol compounds, as shown in the following scheme 8. The alcohol compound represented by formula (9-a) and the alcohol compound represented by formula (9-b) may be simultaneously subjected to a vinylation reaction, as shown in the following scheme 8, or may each be independently subjected to a vinylation reaction.

Scheme 8

[Chemical Formula 25]

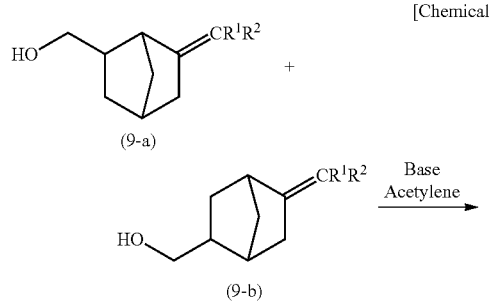

-continued

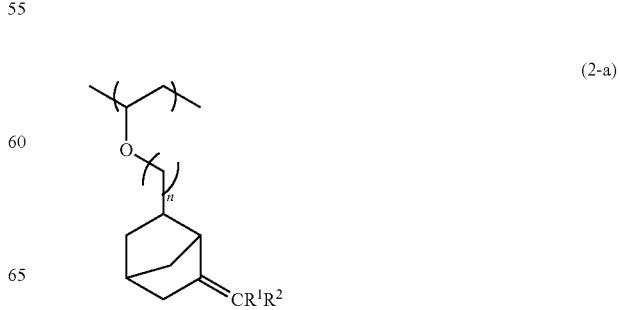

The reaction shown in the scheme 8 can be performed in the presence of a solvent or without a solvent. Here, examples of the solvent include aprotic solvents, such as 1,3-dimethyl-2-imidazolidinone, diglyme, triglyme, and tetraglyme. These may be used alone, or two or more may be mixed and used.

The used amount of the aprotic solvent is preferably 1 to 20 moles, more preferably 3 to 13 moles, with respect to 1 mole of the alcohol compounds represented by formula (9-a) and/or formula (9-b).

In the reaction shown in the scheme 8, examples of the base include alkali metal hydroxides, such as sodium hydroxide and potassium hydroxide; and alkaline-earth metal hydroxides, such as magnesium hydroxide, calcium hydroxide, and barium hydroxide, and among these, alkali metal hydroxides, such as sodium hydroxide and potassium hydroxide, are preferred.

The used amount of the base is preferably 0.05 to 1 mole with respect to 1 mole of the alcohol compounds represented by formula (9-a) and/or formula (9-b), and more preferably 0.1 to 0.5 moles from reaction rate and economical viewpoints.

The acetylene used in the scheme 8 is preferably introduced into a reaction container so that gauge pressure is 0.01 MPa or more, and is more preferably introduced into a reaction container so that gauge pressure is 0.15 MPa or more, in terms of reaction rate and yield.

The reaction temperature of the reaction shown in the scheme 8 is preferably 80 to 180° C., more preferably 100 to 140° C.

[Vinyl Ether Polymer]

A vinyl ether polymer according to this embodiment comprises a structural unit represented by formula (2-a) and/or a structural unit represented by formula (2-b).

[Chemical Formula 26]

(2-b)

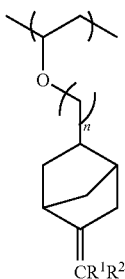

[Chemical Formula 28]

(2-a-1)

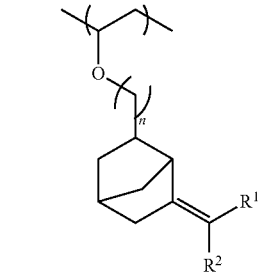

wherein n represents 0 or 1, and $R^1$ and $R^2$ each independently represent a hydrogen atom, a methyl group, or an ethyl group, provided that the total of the number of carbon atoms of $R^1$ and the number of carbon atoms of $R^2$ is 1 or 2.

If n is 2 or more, a result is that a norbornane skeleton considered to provide heat resistance and low moisture absorbency is away from the polymer main chain of the vinyl ether polymer. Therefore, if n is 2 or more, a tendency is seen that a decrease in the heat resistance and an increase in the moisture absorbency of the vinyl ether polymer are caused, and the thermal stability and shape retention properties of the vinyl ether polymer are poor, compared with a case where n is 0 or 1.

n is preferably 0, Such a vinyl ether polymer is better in heat resistance and shape retention properties.

n being 0 indicates that an oxygen atom and a norbornane skeleton in the formulas are directly bonded to each other. In other words, when n is 0, the above structural units are represented by formula (2-c) or formula (2-d). In the formulas, $R^1$ and $R^2$ have the same meanings as the above.

(2-a-2)

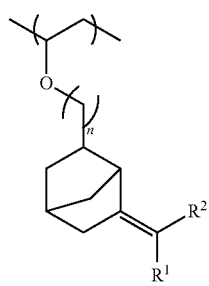

[Chemical Formula 27]

(2-c)

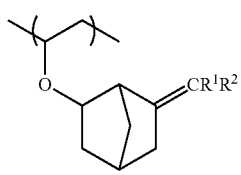

(2-b-1)

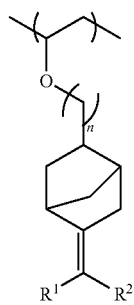

(2-d)

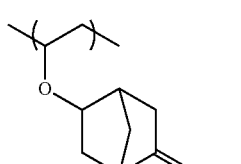

(2-b-2)

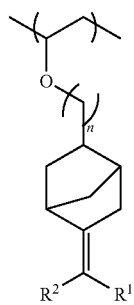

Examples of the structural unit represented by formula (2-a) include a structural unit represented by formula (2-a-1) and a structural unit represented by formula (2-a-2). In addition, examples of the structural unit represented by formula (2-b) include a structural unit represented by formula (2-b-1) and a structural unit represented by formula (2-a-2).

The vinyl ether polymer according to this embodiment may contain the above structural units at any content ratio. In addition, the vinyl ether polymer has the above-described effect when it has any of the above structural units.

The vinyl ether polymer according to this embodiment may be a homopolymer of the above vinyl ether compounds, that is, a polymer produced by a polymerization reaction using the above vinyl ether compounds as monomers. Such a vinyl ether polymer is represented, for example, by formula (10).

[Chemical Formula 29]

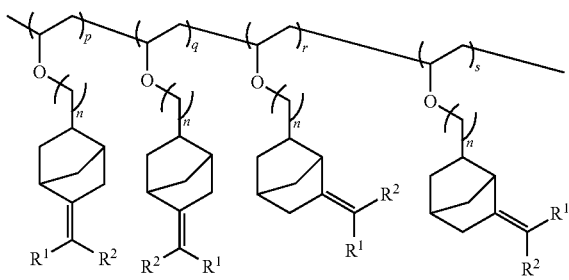

(10)

wherein $R^1$, $R^2$, and n have the same meanings as the above, and p, q, r, and s each independently represent an integer of 0 or more, provided that p+q+r+s is 2 or more.

The polymerization degree of the vinyl ether polymer according to this embodiment can be 2 to 10000. In the vinyl ether polymer represented by formula (10), the polymerization degree being 2 to 10000 means the same as p+q+r+s being 2 to 10000.

In addition, the vinyl ether polymer according to this embodiment may be a copolymer of the above vinyl ether compounds and another monomer.

Examples of such a copolymer include a vinyl ether polymer containing the structural unit represented by formula (2-a) and/or the structural unit represented by formula (2-b), and a structural unit represented by formula (3) (hereinafter sometimes referred to as an "isobutylene-based polymer").

[Chemical Formula 30]

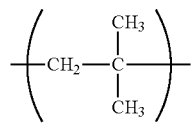

(3)

Examples of the above isobutylene-based polymer include a copolymer of the above vinyl ether compounds with isobutylene. Such an isobutylene-based polymer is represented, for example, by formula (11).

[Chemical Formula 31]

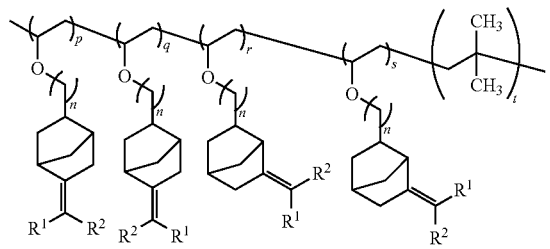

(11)

wherein $R^1$, $R^2$, and n have the same meanings as the above, p, q, r, and s each independently represent an integer of 0 or more, and t represents an integer of 1 or more, provided that p+q+r+s is 1 or more.

The polymerization degree of the isobutylene-based polymer can be 2 to 10000. In the isobutylene-based polymer represented by formula (11), the polymerization degree being 2 to 10000 means the same as p+q+r+s+t being 2 to 10000.

The isobutylene-based polymer can be produced, for example, by a copolymerization reaction using the above vinyl ether compounds and isobutylene as monomers.

(Method for Producing Vinyl Ether Polymer)

The vinyl ether polymer according to this embodiment can be obtained by a polymerization reaction using the above vinyl ether compounds as monomers. The polymerization reaction can be performed, for example, by performing cationic polymerization in the presence of a Lewis acid (polymerization catalyst). The vinyl ether polymer obtained in this manner is excellent in transparency and electrical conductivity, and is useful in the field of optical materials. In addition, the vinyl ether polymer can exhibit excellent performance also in electronic and electrical fields of semiconductor sealing materials, insulating coating materials, and the like. Further, moisture absorbency is low, and therefore, dimensional stability in use as industrial materials is good; and the vinyl ether polymer is excellent in moisture resistance, and therefore, it can be stably used for a long period even in outdoors and the like.

In the above polymerization reaction, it is possible to use a cationically polymerizable compound, such as isobutylene, with the above vinyl ether compounds, as monomers. Thus, it is possible to obtain a vinyl ether polymer, such as the above isobutylene-based polymer.

As the above Lewis acid, a wide range of Lewis acids can be used from among publicly known ones that can be used in cationic polymerization. Examples of the Lewis acids include, but not limited to, boron halide compounds, such as boron trichloride, boron trifluoride, and a diethyl ether complex and methanol complex of boron trifluoride; titanium halide compounds, such as titanium tetrachloride, titanium tetrabromide, and titanium tetraiodide; tin halide compounds, such as tin tetrachloride, tin tetrabromide, and tin tetraiodide; aluminum halide compounds, such as aluminum trichloride, alkyldichloroaluminum, and dialkylchloroaluminum; antimony halide compounds, such as antimony pentachloride and antimony pentafluoride; tungsten halide compounds, such as tungsten pentachloride; molybdenum halide compounds, such as molybdenum pentachloride; tantalum halide compounds, such as tantalum pentachloride; and metal alkoxides, such as tetraalkoxytitanium. Among these Lewis acids, boron trifluoride, aluminum trichloride, ethyldichloroaluminum, tin tetrachloride, titanium tetrachloride, and the like are preferred. For the used amount of the Lewis acid, 0.01 to 1000 millimolar equivalents can be used with respect to 1 mole of the monomers of the raw materials, and the used amount of the Lewis acid is preferably in the range of 0.05 to 500 millimolar equivalents.

Further, it is also possible to allow an electron donor component to coexist when performing living cationic polymerization, as required. This electron donor component is considered to have the effect of stabilizing growing carbon cations and/or the effect of trapping protons in a system, in cationic polymerization, and by the addition of electron donors, a polymer having a controlled structure and a narrow molecular weight distribution is produced. The electron donor component that can be used is not particularly limited, and conventionally publicly known ones can be widely used as long as the number of donors is 15 to 60. Examples thereof include pyridines, such as α-picoline and di-t-butylpyridine, amines, such as triethylamine, amides, such as dimethylacetamide, sulfoxides, such as dimethyl sulfoxide, esters, phosphorus compounds, or metal compounds having an oxygen atom bonded to a metal atom, such as tetraisopropoxytitanium.

In addition, it is possible to use a reaction solvent in the above cationic polymerization. Examples of the reaction solvent include a single solvent selected from the group consisting of halogenated hydrocarbons, aliphatic hydrocarbons, and aromatic hydrocarbons, or a mixed solvent thereof.

As the halogenated hydrocarbons, chloroform, methylene chloride, 1,1-dichloroethane, 1,2-dichloroethane, n-propyl chloride, n-butyl chloride, 1-chloropropane, 1-chloro-2-methylpropane, 1-chlorobutane, 1-chloro-2-methylbutane, 1-chloro-3-methylbutane, 1-chloro-2,2-dimethylbutane, 1-chloro-3,3-dimethylbutane, 1-chloro-2,3-dimethylbutane, 1-chloropentane, 1-chloro-2-methylpentane, 1-chloro-3-methylpentane, 1-chloro-4-methylpentane, 1-chlorohexane, 1-chloro-2-methylhexane, 1-chloro-3-methylhexane, 1-chloro-4-methylhexane, 1-chloro-5-methylhexane, 1-chloroheptane, 1-chlorooctane, 2-chloropropane, 2-chlorobutane, 2-chloropentane, 2-chlorohexane, 2-chloroheptane, 2-chlorooctane, chlorobenzene, and the like can be used, and a solvent selected from among these may be single or may be one composed of two or more components.

As the aliphatic hydrocarbons, propane, butane, pentane, neopentane, hexane, heptane, octane, cyclohexane, methylcyclohexane, and ethylcyclohexane are preferred, and a solvent selected from among these may be single or may be one composed of two or more components.

As the aromatic hydrocarbons, benzene, toluene, xylene, and ethylbenzene are preferred, and a solvent selected from among these may be single or may be one composed of two or more components.

In the above cationic polymerization, when using the reaction solvent, it is preferred to, considering the solubility of the obtained polymer, the viscosity of a solution, and the ease of heat removal, use the solvent so that the concentration of the polymer is 0.1 to 80% by mass, and in terms of production efficiency and operability, it is more preferred to use the solvent so that the concentration of the polymer is 1 to 50% by mass. In addition, as monomer concentration during the polymerization, about 0.1 to 8 moles/liter is preferred, and about 0.5 to 5 moles/liter is more preferred. In addition, the used amount of the organic solvent during the polymerization is preferably 0.5 to 100 times amount, with respect to the monomers used, in terms of appropriate viscosity and the control of heat generation.

For various raw materials used in the above cationic polymerization, industrially or experimentally available ones can be used, but if substances having active hydrogen, such as water, alcohols, and hydrochloric acid, and compounds having a chlorine atom bonded to tertiary carbon, other than an initiator, are contained in the raw materials, these become the causes of producing side reactions as impurities, and therefore, it is necessary to previously perform purification at concentrations as low as possible. In addition, it is necessary to prevent these impurities from entering from outside during the operation of the reaction. In order to efficiently obtain the target polymer, it is preferred to control the total number of moles of the impurities to 1 time or less, based on the total number of the polymerization start points of the initiator, and it is more preferred to control the total number of moles of the impurities to 0.5 times or less.

The above cationic polymerization is preferably performed under an atmosphere of an inert gas, such as nitrogen, argon, or helium. For pressure during the polymerization, it is possible to adopt any condition, such as atmospheric pressure or applied pressure, considering the type of the monomers, the type of the organic solvent, polymerization temperature, and the like. In addition, it is preferred to perform polymerization under sufficient stirring conditions so that a polymerization system is uniform. The above cationic polymerization can be performed, for example, by a batch method or semibatch method of sequentially feeding the polymerization solvent, the monomers, the catalyst, and an initiator and chain transfer agent and the like as required, to one reaction container. Alternatively, the above cationic polymerization may be performed by a continuous method in which a reaction is performed while the polymerization solvent, the monomers, the catalyst, and an initiator and chain transfer agent and the like as required are continuously fed into a certain system, and further a product is removed. The batch method is preferred in that it is easy to control a polymerization start time point, and the concentration of the polymerization catalyst during the polymerization, and so on.

Polymerization temperature affects the average molecular weight of the obtained vinyl ether-based polymer, and therefore, polymerization temperature adopted should be appropriately selected according to a target average molecular weight, and polymerization temperature is preferably about −80° C. to 20° C., and further preferably about −70 to 0° C., and polymerization time is generally about 0.5 to 180 minutes, preferably about 20 to 150 minutes.

In the above cationic polymerization, it is preferred to stop the polymerization reaction by the addition of alcohols, such as methanol, for subsequent ease of handling, but a method for stopping the polymerization reaction is not particularly limited to this, and it is possible to apply any of conventional common means, and it is not necessary to particularly perform a stop reaction anew.

The form of a reactor used in the above cationic polymerization is not particularly limited, but a stirred tank reactor is preferred. Its structure is not particularly limited, but is preferably, for example, a structure that has a structure in which cooling in a jacket portion is possible, and that can uniformly mix and react the monomers, and the catalyst and an electron donating agent sequentially supplied. The structure may be a structure in which accessory equipment, such as an internal cooling coil and a reflux condenser, is provided to improve cooling ability, and a baffle can be provided to make a mixed state good. A stirring blade used in the stirred tank reactor is not particularly limited, but is preferably one in which the performance of the vertical circulation and mixing of a reaction liquid is high, and stirring blades, such as a (multistage) inclined paddle blade and a turbine blade, are preferably used in a relatively low viscosity region in which polymerization and reaction liquid viscosity is about several centipoises, large blades having large bottom paddles, such as a MAXBLEND blade, a FULLZONE blade, a SANMELER blade, a Hi-F mixer blade, and one described in Japanese Patent Application Laid-Open Publication No. 10-24230, are preferably used in a medium viscosity region in which the polymerization and reaction liquid viscosity is several tens of centipoises to several hundreds of poises, and an anchor blade, a (double) helical ribbon blade, a LOGBORN blade, and the like are preferably used in a high viscosity region in which the polymerization and reaction liquid viscosity is several hundreds of poises or more.

EXAMPLES

The present invention will be specifically described below by Examples, but the present invention is not limited to these Examples.

Example 1

(Production of Ethylidene Norbornanols)

As a synthesis apparatus, a four-neck separable flask having an internal volume of 5000 mL, equipped with a revolution number-variable stirrer, a reaction temperature indicator, a reaction dropping port, a reflux tube, and a gas injection port, was placed in a heating medium bath in which temperature control is possible. 228.5 g (1.9 mol) of 5-ethylidene-2-norbornene (manufactured by Nippon Oil Corporation), 2000 mL of toluene (a special grade reagent, manufactured by Wako Pure Chemical Industries, Ltd.), and 342 g (5.7 mol) of acetic acid (a special grade reagent, manufactured by KANTO CHEMICAL CO., INC.) were added, in order, to the flask, and liquid temperature was maintained at 90° C.

While the fed mixture was stirred, 49 g (0.5 mol) of sulfuric acid (a special grade reagent, manufactured by Wako Pure Chemical Industries, Ltd.) was dropped from a dropping funnel provided in the reaction dropping port in 5 minutes, and the mixture was stirred at a liquid temperature of 107° C. for 90 minutes. After the disappearance of 5-ethylidene-2-norbornene was confirmed by gas chromatograph analysis, the reaction mixture was cooled to 50 degrees, then, 427 g (7.6 mol) of potassium hydroxide (a special grade reagent, manufactured by KANTO CHEMICAL CO., INC.) and 800 mL of ethanol (95%, manufactured by KANTO CHEMICAL CO., INC.) were gradually added, and the mixture was stirred at a liquid temperature of 90° C. for 1 hour.

The reaction liquid was cooled to room temperature, and then, the reaction liquid was poured into a 5000 mL beaker containing 2500 mL of a saturated saline solution. Then, a separated organic layer was transferred to a separatory funnel, washed with a saturated saline solution again, and dried with magnesium sulfate. The magnesium sulfate was filtered using a Kiriyama funnel equipped with Kiriyama filter paper, and the solvent of the filtrate was removed by an evaporator to obtain crude products of 5-ethylidene-2-norbornanol and 5-ethylidene-3-norbornanol.

Then, reduced pressure distillation was performed for the obtained crude products, and a fraction at a reduced pressure of 2 mmHg and a temperature of 84 to 85° C. was collected to obtain 59.1 g of a mixture of 5-ethylidene-2-norbornanol and 5-ethylidene-3-norbornanol (hereinafter referred to as a "mixture of ethylidene norbornanols") as a colorless transparent liquid.

[Chemical Formula 32]

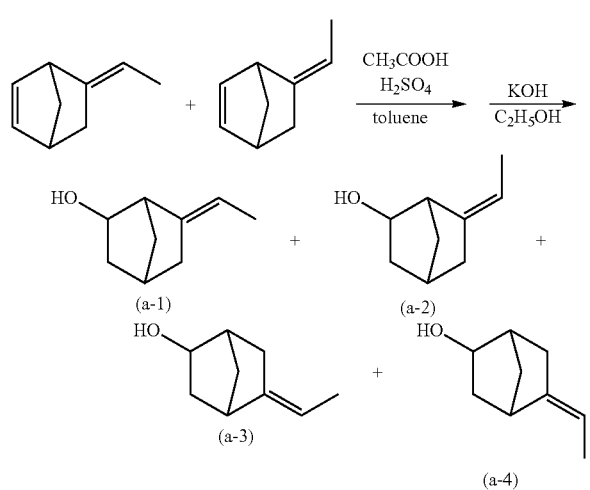

For the obtained mixture of ethylidene norbornanols, structure analysis was performed by gas chromatograph-mass spectrum (GC-MS), IR analysis, and NMR analysis, and it was confirmed that a mixture of isomers of ethylidene norbornanol represented by formula (a-1) to formula (a-4) was produced. Analysis results are shown below.

(Analysis Results)
GC-MS measurement [M/Z]: 138
IR measurement detected wave numbers (cm$^{-1}$): 3328, 2960

$^1$H-NMR measurement [499.75 MHz, CDCl$_3$, internal 0 standard TMS]: When a chemical shift (PPM), a splitting pattern, and the number of protons were measured, signals corresponding to the ethylidene norbornanol isomers represented by formula (a-1) to formula (a-4) were observed, and among them, two types were mainly observed. Obtained results are shown in Table 1.

TABLE 1

| Main product 1<br>PPM (Splitting pattern,<br>the number of protons) | Main product 2<br>PPM (Splitting pattern,<br>the number of protons) |
|---|---|
| 1.21-2.10 (m, 9H) | 1.21-2.10 (m, 9H) |
| 2.32-2.43 (m, 2H) | 2.32-2.43 (m, 2H) |
| 2.57 (br, 1H) | 2.86 (br, 1H) |
| 3.80 (br, 1H) | 3.80 (br, 1H) |
| 5.39 (br, 1H) | 5.19 (br, 1H) |

$^{13}$C-NMR measurement [125.66 MHz, CDCl$_3$, internal 0 standard: TMS]: When a chemical shift (PPM) and a carbon class were measured, signals corresponding to the ethylidene norbornanol isomers represented by formula (a-1) to formula (a-4) were observed, and among them, two types were mainly observed. Obtained results are shown in Table 2. The carbon class was determined by NMR analysis using a DEPT measurement method. S, D, T, and Q represent primary, secondary, tertiary, and quaternary carbons, respectively.

TABLE 2

| Main product 1<br>PPM (Carbon class) | Main product 2<br>PPM (Carbon class) |
|---|---|
| 14.0 (S) | 14.6 (S) |
| 34.5 (D) | 34.8 (D) |
| 35.2 (D) | 35.6 (T) |
| 35.7 (T) | 37.5 (D) |
| 41.3 (D) | 41.2 (D) |
| 53.5 (T) | 48.2 (T) |
| 74.2 (T) | 74.2 (T) |
| 114.7 (T) | 115.5 (T) |
| 141.3 (Q) | 140.3 (Q) |

(Production of Ethylidene Norbornyl-Vinyl Ethers)

The production of ethylidene norbornyl-vinyl ethers was performed using the above mixture of ethylidene norbornanols.

First, as a synthesis apparatus, a four-neck flask having an internal volume of 2000 mL, equipped with a revolution number-variable stirrer, a reaction temperature indicator, a reaction dropping port, a reflux tube, and a gas injection port, was placed in a heating medium bath in which temperature control is possible.

66.9 g (631 mmol) of sodium carbonate (a special grade reagent, manufactured by Wako Pure Chemical Industries, Ltd.) and 500 mL of toluene (a dehydrating reagent, manufactured by KANTO CHEMICAL CO., INC.) were placed in the flask, and heated to a liquid temperature of 90° C. 108.65 g (1262 mmol) of vinyl acetate (manufactured by TOKYO CHEMICAL INDUSTRY CO., LTD.) was added to the flask, and further, 9.4 mL (126 mmol) of propionic acid (manufactured by TOKYO CHEMICAL INDUSTRY CO., LTD.) was dropped over 5 minutes. After the dropping, 8.0 g (11.90 mmol) of an [IrCl(cod)]$_2$ catalyst (manufactured by Wako Pure Chemical Industries, Ltd.) was added, further, 87.2 g (631 mmol) of the mixture of ethylidene norbornanols dissolved in 500 mL of 1,4-dioxane (a dehydrating reagent, manufactured by KANTO CHEMICAL CO., INC.) was dropped over 1 hour, and the mixture was stirred for 8 hours.

Then, the reaction liquid was cooled to room temperature, poured into a beaker containing water, and extracted with ethyl acetate (manufactured by Godo Co., Ltd.) 3 times. Then, an obtained organic phase was washed with water 2 times, and dried with sodium sulfate (a reagent special grade, manufactured by NACALAI TESQUE, INC.), then, the sodium sulfate was filtered using a Kiriyama funnel equipped with Kiriyama filter paper, and the solvent of the filtrate was removed by an evaporator to obtain 120.12 g of a blackish brown oily crude product. Reduced pressure distillation was performed for the obtained crude product, and a fraction at a reduced pressure of 100 Pa and a temperature of 43 to 45° C. was collected to obtain 78.36 g of a target mixture of ethylidene norbornyl-vinyl ethers as a colorless transparent liquid.

[Chemical Formula 33]

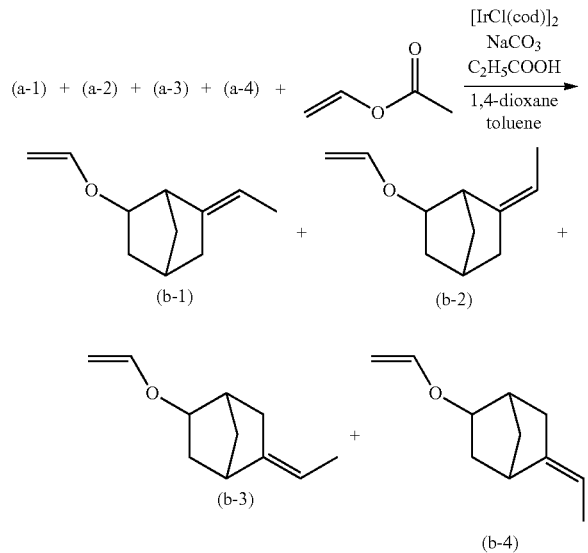

For this product, structure analysis was performed by gas chromatograph-mass spectrum (GC-MS), IR analysis, elementary analysis, and NMR analysis, and it was confirmed that isomers of ethylidene norbornyl-vinyl ether represented by formula (b-1) to formula (b-4) were produced. Analysis results are shown below.

(Analysis Results)

GC-MS measurement [M/Z]: 164

IR measurement detected wave number (cm$^{-1}$): 2965

Elementary analysis: measured values C, 80.0; H, 9.7 (theoretical values C, 80.4; H, 9.8).

$^1$H-NMR measurement [499.75 MHz, CDCl$_3$, internal 0 standard TMS]: When a chemical shift (PPM), a splitting pattern, and the number of protons were measured, signals corresponding to the isomers of ethylidene norbornyl-vinyl ether represented by formula (b-1) to formula (b-4) were observed, and among them, two types were mainly observed. Obtained results are shown in Table 3.

TABLE 3

| Main product 1<br>PPM (Splitting pattern,<br>the number of protons) | Main product 2<br>PPM (Splitting pattern,<br>the number of protons) |
| --- | --- |
| 1.29-1.31 (m, 1H) | 1.29-1.31 (m, 1H) |
| 1.48-2.13 (m, 9H) | 1.48-2.13 (m, 9H) |
| 2.44 (br, 1H) | 2.38 (br, 1H) |
| 2.79 (br, 1H) | 3.11 (br, 1H) |
| 3.85-4.01 (m, 2H) | 3.85-4.01 (m, 2H) |
| 4.13-4.21 (m, 1H) | 4.13-4.21 (m, 1H) |
| 5.42-5.45 (m, 1H) | 5.22-5.26 (m, 1H) |
| 6.23-6.37 (m, 1H) | 6.23-6.37 (m, 1H) |

$^{13}$C-NMR measurement [125.66 MHz, CDCl$_3$, internal 0 standard TMS]: When a chemical shift (PPM) and a carbon class were measured, signals corresponding to the isomers of ethylidene norbornyl-vinyl ether represented by formula (b-1) to formula (b-4) were observed, and among them, two types were mainly observed. Obtained results are shown in Table 4. The carbon class was determined by NMR analysis using a DEPT measurement method. S, D, T, and Q represent primary, secondary, tertiary, and quaternary carbons, respectively.

TABLE 4

| Main product 1<br>PPM (Carbon class) | Main product 2<br>PPM (Carbon class) |
| --- | --- |
| 14.1 (S) | 14.7 (S) |
| 34.8 (D) | 35.5 (D) |
| 35.7 (T) | 35.6 (T) |
| 35.8 (D) | 37.9 (D) |
| 38.8 (D) | 38.6 (T) |
| 50.0 (T) | 44.8 (T) |
| 80.2 (T) | 79.1 (T) |
| 87.7 (D) | 87.6 (D) |
| 115.5 (T) | 116.2 (T) |
| 140.8 (Q) | 139.8 (Q) |
| 150.2 (T) | 150.2 (T) |

Example 2

The production of a polymer of ethylidene norbornyl-vinyl ether was performed using the mixture of ethylidene norbornyl-vinyl ethers obtained in Example 1.

A three-neck flask having an internal volume of 50 mL, equipped with a reaction temperature indicator, a reaction dropping port, and a gas injection port, was used as a synthesis apparatus, and nitrogen was allowed to flow for 10 minutes to make the inside of the flask be under a nitrogen atmosphere. A stirrer, 1.68 g (10.2 mmol) of the mixture of ethylidene norbornyl-vinyl ethers, and 10 mL of toluene distilled according to a conventional method were added to the flask, and the flask was immersed in a dry ice-methanol bath to cool contents to −68° C. Then, 0.02 equivalents (26 µL) of a boron trifluoride.diethyl ether complex (manufactured by TOKYO CHEMICAL INDUSTRY CO., LID.) was dropped. At the time, the increase of contents temperature was seen up to −65° C. Then, the contents were stirred for 2 hours while the temperature was gradually increased to 0° C., 3 drops of a 28% to 30% ammonia aqueous solution (manufactured by KANTO CHEMICAL CO., INC.) were added, and the mixture was stirred for 10 minutes. When the mixture was dropped into methanol filling a 500 mL beaker, a precipitate formed, and by collecting the precipitate by the filtration operation of a Kiriyama funnel, 1.21 g (yield 72%) of a polymer of ethylidene norbornyl-vinyl ether was obtained.

[Chemical Formula 34]

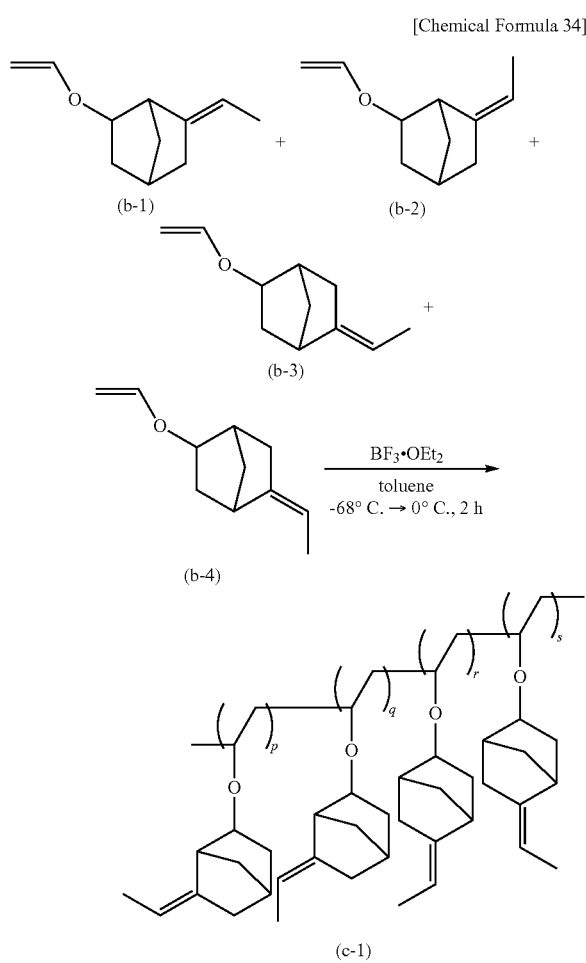

For the obtained polymer, structure analysis was performed by nuclear magnetic resonance spectroscopy (NMR), and it was confirmed that a polymer represented by formula (c-1) was obtained. In $^1$H-NMR measurement, the signal (6.23 to 6.37 ppm) derived from vinyl ether in the ethylidene norbornyl-vinyl ether disappeared, the signal of an ethylidene group was observed at 5.00 to 5.35 ppm, and a proton at the α-position of ether oxygen was observed at 3.50 ppm. The conditions of the $^1$H-NMR measurement were 499.75 MHz, CDCl$_3$, and internal 0 standard TMS.

In addition, its molecular weight was measured by gel permeation chromatography (GPC). For the measured molecular weight, a number-average molecular weight (Mn) was 8050, and a weight-average molecular weight (Mw) was 16946, and Mw/Mn was 2.105.

Example 3

The production of a polymer of ethylidene norbornyl-vinyl ether was performed under reaction conditions different from those of Example 2, using the mixture of ethylidene norbornyl-vinyl ethers obtained in Example 1.

A three-neck flask having an internal volume of 50 mL, equipped with a reaction temperature indicator, a reaction dropping port, and a gas injection port, was used as a synthesis apparatus, and nitrogen was allowed to flow for 10 minutes to make the inside of the flask be under a nitrogen atmosphere. A stirrer, 251 mg (1.53 mmol) of the mixture of ethylidene norbornyl-vinyl ethers, and 1.5 mL of toluene distilled by a conventional method were added to the flask, and the flask was immersed in a common salt-ice water bath to cool contents to −9° C. Then, 0.05 equivalents (1.3 mL) of ethylaluminum dichloride (0.057 M, an isooctane solution (prepared from a product manufactured by Aldrich)) was dropped. At the time, contents temperature increased to −6° C. Then, the contents were stirred for 1 hour and a half while the temperature was gradually increased to 0° C., and 3 drops of a 28% to 30% ammonia aqueous solution (manufactured by KANTO CHEMICAL CO., INC.) were added. By dropping the mixture into methanol filling a 100 mL beaker, a precipitate formed, and by collecting the precipitate, 34 mg (yield 21%) of a polymer of ethylidene norbornyl-vinyl ether was obtained.

For the obtained polymer, structure analysis was performed by nuclear magnetic resonance spectroscopy (NMR), and it was confirmed that a polymer of ethylidene norbornyl-vinyl ether was obtained. In $^1$H-NMR measurement, the signal (6.23 to 6.37 ppm) derived from vinyl ether in the ethylidene norbornyl-vinyl ether disappeared, the signal of an ethylidene group was observed at 5.00 to 5.35 ppm, and a proton at the α-position of ether oxygen was observed at 3.50 ppm. The conditions of the $^1$H-NMR measurement were 499.75 MHz, CDCl$_3$, and internal 0 standard TMS.

In addition, its molecular weight was measured by gel permeation chromatography (GPC). For the measured molecular weight, a number-average molecular weight (Mn) was 2529, and a weight-average molecular weight (Mw) was 3727, and Mw/Mn was 1.474.

Example 4

The production of an isobutylene-based polymer was performed using the mixture of ethylidene norbornyl-vinyl ethers obtained in Example 1, and isobutylene.

A septum cap, a reflux tube to which a vacuum line was connected, and a temperature tube were attached to a 100 mL three-neck flask, a stirrer bar was placed in the flask, and degassing-nitrogen replacement in the system was repeated 2 times, using a vacuum line (with a Schlenk tube), to make the inside of the system be under an atmospheric pressure nitrogen atmosphere. A predetermined amount of a toluene solvent dried with calcium hydride and distilled was injected into the flask from the septum cap, using a syringe.

Next, the mixture of ethylidene norbornyl-vinyl ethers in a predetermined molar amount described in the following Table 5 was injected using a syringe. The flask was immersed in a low temperature tank (calcium chloride-water-ice bath) at a predetermined temperature, and after it was confirmed that liquid temperature in the system reached a predetermined temperature described in Table 5, isobutylene measured in a predetermined molar amount described in Table 5 was transferred to the reaction system.

At a point of time when the liquid temperature in the system sufficiently reached the predetermined temperature described in Table 5, a catalyst liquid prepared by diluting a 1.06 mol/L ethylaluminum dichloride (hereinafter sometimes referred to as "EADC") n-hexane solution 10 times with purified hexane in a glove box under a nitrogen atmosphere was measured by a syringe, and injected into the reactor.

After 2 hours from the catalyst liquid injection, the low temperature tank was removed from the flask, and the flask was allowed to stand to room temperature. The reaction mixture was subjected to an extraction operation with a 1 N sodium hydroxide aqueous solution (2 times), and an obtained oil phase was subjected to an extraction operation with pure water. After it was confirmed that pH on an aqueous phase side became neutral, the solvent was distilled off by an evaporator, and a residue was dried at 1 mmHg and 60° C. for 12 hours with a reduced pressure dryer to obtain a target copolymer of isobutylene.

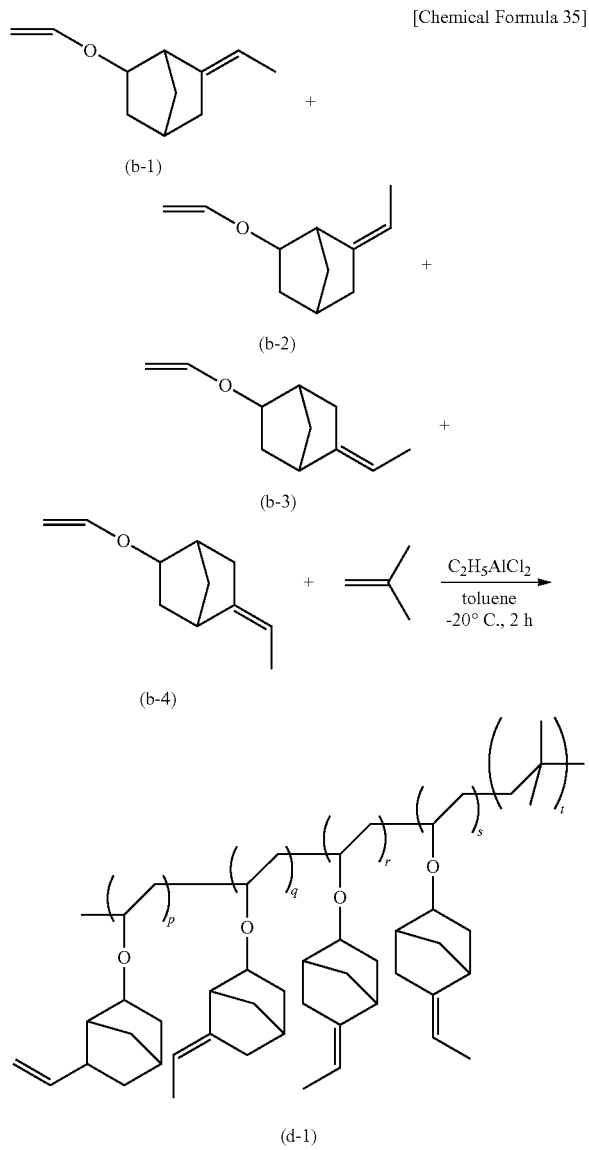

For the obtained copolymer, structure analysis was performed by nuclear magnetic resonance spectroscopy (NMR), and it was confirmed that an isobutylene-based polymer represented by formula (d-1) was obtained. In $^1$H-NMR measurement, the signal (6.23 to 6.37 ppm) derived from vinyl ether in the ethylidene norbornyl-vinyl ether disappeared, the signal of an ethylidene group was observed at 5.00 to 5.35 ppm, and a proton at the α-position of ether oxygen was observed at 3.50 ppm. The conditions of the $^1$H-NMR measurement were 499.75 MHz, CDCl$_3$, and internal 0 standard TMS. In $^{13}$C-NMR measurement, a signal derived from carbon at the α-position of ether oxygen was observed at 78.9 ppm, a signal derived from the tertiary carbon of the ethylidene group was observed at 111.3 to 115.0 ppm, and a signal derived from the quaternary carbon of the ethylidene group was observed at 141.2 to 145.1 ppm. The conditions of the $^{13}$C-NMR measurement were 125.66 MHz, CDCl$_3$, and internal 0 standard TMS.

For the obtained isobutylene-based polymer, a weight-average molecular weight was measured by gel permeation chromatography (GPC), and a copolymerization introduction ratio was calculated from the results of the $^1$H-NMR measurement. In addition, the glass transition temperature of the obtained isobutylene-based polymer was measured. Measurement results were as shown in Table 5.

Examples 5 to 7

Isobutylene-based polymers were obtained as in Example 4 except that the feed ratio of isobutylene to vinyl ethers, an EADC catalyst amount, reaction temperature, and yield were changed as described in Table 5. For the obtained respective isobutylene-based polymers, structure analysis was performed by nuclear magnetic resonance spectroscopy (NMR), and it was confirmed that target polymers were obtained. In addition, the measurement of a weight-average molecular weight by gel permeation chromatography (GPC), the calculation of a copolymerization introduction ratio by the analysis of the results of $^1$H-NMR measurement, and the measurement of glass transition temperature were performed. For the measurement of glass transition temperature, measurement was repeatedly performed 2 times for a temperature range of −100 to 230° C. at a temperature increase rate of 20° C./min under a nitrogen atmosphere, using Diamond DSC manufactured by PerkinElmer, and the second detected temperature was determined as the glass transition temperature of a sample of interest. Measurement results were as shown in Table 5.

TABLE 5

| | Example 4 | Example 5 | Example 6 | Example 7 |
|---|---|---|---|---|
| Feed ratio (molar ratio) of isobutylene/vinyl ethers | 95/5 | 90/10 | 85/15 | 85/15 |
| EADC catalyst amount (with respect to % by mass of monomers) | 4.0 | 3.7 | 3.4 | 3.4 |
| Reaction temperature (° C.) | −20 | −30 | −30 | −20 |
| Reaction time (hours) | 2 | 2 | 2 | 2 |
| Yield (%) | 32.3 | 39 | 57.5 | 42 |
| Copolymerization introduction ratio ($^1$H-NMR) | 99/1 | 98/2 | 98/2 | 95/5 |
| GPC-Mw | 5100 | 6300 | 2400 | 1900 |
| Glass transition temperature (° C.) | −63 | −63 | −67 | −40 |

Example 8

A septum cap, a reflux tube to which a vacuum line was connected, and a temperature tube were attached to a 100 mL three-neck flask, a stirrer bar was placed in the flask, and degassing-nitrogen replacement in the system was repeated 2 times, using a vacuum line (with a Schlenk tube), to make the inside of the system be under an atmospheric pressure nitrogen atmosphere. A predetermined amount of a toluene solvent dried with calcium hydride and distilled was injected into the flask from the septum cap, using a syringe.

Next, the mixture of ethylidene norbornyl-vinyl ethers in a predetermined molar amount described in the following Table 6 was injected using a syringe. The flask was immersed in a low temperature tank (calcium chloride-water-ice bath) at a predetermined temperature, and after it was confirmed that liquid temperature in the system reached a predetermined temperature described in Table 6, isobutylene measured in a predetermined molar amount described in Table 6 was transferred to the reaction system.

At a point of time when the liquid temperature in the system sufficiently reached the predetermined temperature described in Table 6, a boron trifluoride methanol complex (the content of $BF_3$ is 67% by mass, hereinafter sometimes referred to as "$BF_3$·MeOH") was measured in a predetermined amount described in Table 6, and injected into the reactor.

After 2 hours from the catalyst liquid injection, the low temperature tank was removed from the flask, and the flask was allowed to stand to room temperature. The reaction mixture was subjected to an extraction operation with a 1 N sodium hydroxide aqueous solution (2 times), and an obtained oil phase was subjected to an extraction operation with pure water. After it was confirmed that pH on an aqueous phase side became neutral, the solvent was distilled off by an evaporator, and a residue was dried at 1 mmHg and 60° C. for 12 hours with a reduced pressure dryer to obtain a target copolymer of isobutylene.

For the obtained copolymer, structure analysis was performed by nuclear magnetic resonance spectroscopy (NMR), and it was confirmed that a target isobutylene-based polymer was obtained. In addition, the measurement of a weight-average molecular weight by gel permeation chromatography (GPC), and the calculation of a copolymerization introduction ratio by the analysis of the results of $^1$H-NMR measurement were performed.

(Sulfur Crosslinkability Test)

For an isobutylene homopolymer (Comparative Example 1, Tetrax 3T, manufactured by Nippon Oil Corporation) and the isobutylene-based polymer of Example 8, sulfur crosslinkability was evaluated, based on viscosity change in dynamic viscoelasticity measurement at constant temperature. The dynamic viscoelasticity measurement was performed using a DAR-50 apparatus manufactured by REOLOGICA INSTRUMENTS AB. A mixture of 1 g of the isobutylene homopolymer or the isobutylene-based polymer, 0.04 g of sulfur as a vulcanizing agent, 0.01 g of NOCCELER CZ-G (manufactured by OUCHI SHINKO CHEMICAL INDUSTRIAL CO., LTD) as a vulcanizing accelerator, 0.03 g of zinc oxide as a vulcanizing accelerating coagent, and 0.02 g of stearic acid was placed in the measurement machine, and for the mixture, temperature was increased from 100° C. to 160° C. at 2° C./min, and after 160° C. was reached, shear viscosity behavior at each temperature was traced while 160° C. was maintained for 30 minutes. Shear viscosity was provided under the conditions of a frequency of 1 Hz and a strain of 10%.

In the case of the isobutylene homopolymer of Comparative Example 1, viscosity increase was not seen in the measurement temperature region. On the other hand, in the case of the isobutylene-based polymer of Example 8, a phenomenon in which viscosity increased suddenly at a predetermined temperature was seen, and sulfur crosslinkability was confirmed. Viscosity increase start temperature is shown in Table 6.

TABLE 6

|  | Comparative Example 1 | Example 8 |
|---|---|---|
| Feed ratio (molar ratio) of isobutylene/vinyl ethers | 100/0 | 95/5 |
| $BF_3$·MeOH catalyst amount (with respect to % by mass of monomers) |  | 1 |

TABLE 6-continued

|  | Comparative Example 1 | Example 8 |
|---|---|---|
| Reaction temperature (° C.) |  | −30 |
| Reaction time (hours) |  | 2 |
| Yield (%) |  | 12 |
| Copolymerization introduction ratio ($^1$H-NMR) | 100/0 | 83/17 |
| GPC-Mw | 35000 | 5600 |
| Sulfur Crosslinking Test (viscosity increase start temperature (° C.)) | Could not be confirmed | 158 |

Industrial Applicability

The vinyl ether polymer of the present invention is excellent in transparency and electrical conductivity and therefore is useful in the field of optical materials, and can exhibit excellent performance also in electronic and electrical fields of semiconductor sealing materials, insulating coating materials, and the like. In addition, the vinyl ether compound of the present invention is useful in producing the above vinyl ether polymer. In addition, a copolymer of the vinyl ether compound of the present invention and isobutylene (isobutylene-based polymer) has sufficient crosslinkability, and is useful in introducing a polyisobutylene skeleton into a rubber composition.

The invention claimed is:

1. A vinyl ether compound represented by formula (1-a) or formula (1-b):

[Chemical Formula 1]

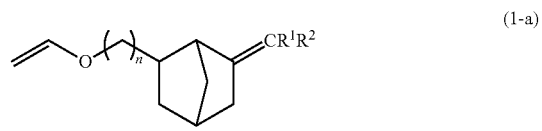

(1-a)

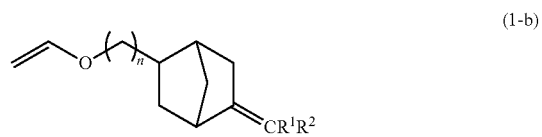

(1-b)

wherein n represents 0 or 1, and $R^1$ and $R^2$ each independently represent a hydrogen atom, a methyl group, or an ethyl group, provided that a total of the number of carbon atoms of $R^1$ and the number of carbon atoms of $R^2$ is 1 or 2.

2. The vinyl ether compound according to claim 1, wherein n is 0.

3. The vinyl ether compound according to claim 1, wherein $R^1$ and $R^2$ are each independently a hydrogen atom or a methyl group, and the total of the number of carbon atoms of $R^1$ and the number of carbon atoms of $R^2$ is 1.

4. A vinyl ether polymer comprising a structural unit represented by formula (2-a) and/or a structural unit represented by formula (2-b):

[Chemical Formula 2]

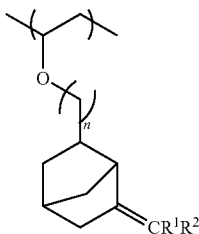
(2-a)

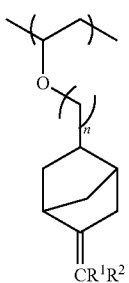
(2-b)

wherein n represents 0 or 1, and $R^1$ and $R^2$ each independently represent a hydrogen atom, a methyl group, or an ethyl group, provided that a total of the number of carbon atoms of $R^1$ and the number of carbon atoms of $R^2$ is 1 or 2.

5. The vinyl ether polymer according to claim 4, wherein n is 0.

6. The vinyl ether polymer according to claim 4, wherein $R^1$ and $R^2$ are each independently a hydrogen atom or a methyl group, and the total of the number of carbon atoms of $R^1$ and the number of carbon atoms of $R^2$ is 1.

7. The vinyl ether polymer according to claim 4, wherein a polymerization degree is 2 to 10000.

8. The vinyl ether polymer according to claim 4, wherein a weight-average molecular weight is 400 to 1000000.

9. The vinyl ether polymer according to claim 4, further comprising a structural unit represented by formula (3):

[Chemical Formula 3]

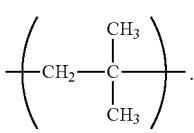
(3)

10. A method for producing a vinyl ether compound, comprising:
a first step of hydrolyzing a compound obtained by reaction of a norbornene compound represented by formula (4) with a carboxylic acid represented by formula (5) in the presence of an acid catalyst, to obtain a norbornanol compound represented by formula (6-a) or formula (6-b); and
a second step of vinylating a hydroxyl group of the norbornanol compound to obtain a vinyl ether compound represented by formula (1-c) or formula (1-d),

[Chemical Formula 4]

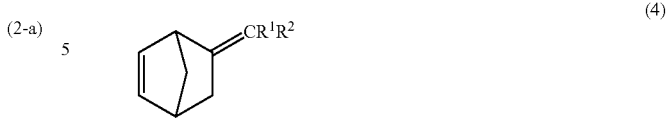
(4)

wherein $R^1$ and $R^2$ each independently represent a hydrogen atom, a methyl group, or an ethyl group, provided that a total of the number of carbon atoms of $R^1$ and the number of carbon atoms of $R^2$ is 1 or 2,

[Chemical Formula 5]

$$R^5\text{—}CO_2H \quad (5)$$

wherein $R^5$ represents an alkyl group having 1 to 20 carbon atoms,

[Chemical Formula 6]

(6-a)

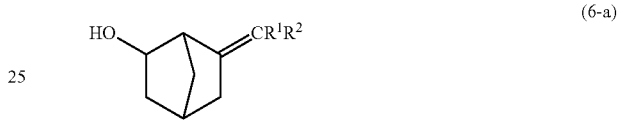
(6-b)

wherein $R^1$ and $R^2$ each independently represent a hydrogen atom, a methyl group, or an ethyl group, provided that a total of the number of carbon atoms of $R^1$ and the number of carbon atoms of $R^2$ is 1 or 2,

[Chemical Formula 7]

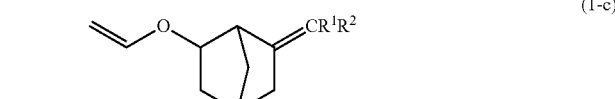
(1-c)

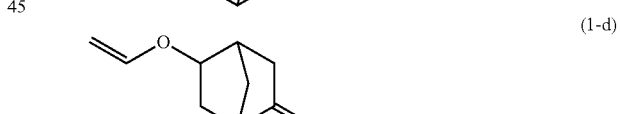
(1-d)

wherein $R^1$ and $R^2$ each independently represent a hydrogen atom, a methyl group, or an ethyl group, provided that a total of the number of carbon atoms of $R^1$ and the number of carbon atoms of $R^2$ is 1 or 2.

11. The method according to claim 10, wherein $R^1$ and $R^2$ are each independently a hydrogen atom or a methyl group, and the total of the number of carbon atoms of $R^1$ and the number of carbon atoms of $R^2$ is 1.

12. The vinyl ether compound according to claim 2, wherein $R^1$ and $R^2$ are each independently a hydrogen atom or a methyl group, and the total of the number of carbon atoms of $R^1$ and the number of carbon atoms of $R^2$ is 1.

13. The vinyl ether polymer according to claim 5, wherein $R^1$ and $R^2$ are each independently a hydrogen atom or a methyl group, and the total of the number of carbon atoms of $R^1$ and the number of carbon atoms of $R^2$ is 1.

14. The vinyl ether polymer according to claim 5, further comprising a structural unit represented by formula (3):
[Chemical Formula 3]
(3)
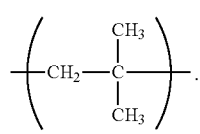
15. The vinyl ether polymer according to claim 13, further comprising a structural unit represented by formula (3):
[Chemical Formula 3]
(3)
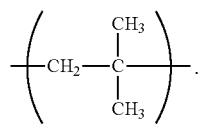
\* \* \* \* \*